United States Patent
Yin et al.

(10) Patent No.: US 12,422,370 B2
(45) Date of Patent: Sep. 23, 2025

(54) BIOMOLECULAR IMAGE SENSOR AND METHOD THEREOF FOR DETECTING BIOMOLECULE

(71) Applicant: Guangzhou Tyrafos Semiconductor Technologies Co., Ltd., Guangzhou (CN)

(72) Inventors: Ping-Hung Yin, Taipei (TW); Jun-Wen Chung, Tainan (TW); Chun-I Shao, Taitung County (TW); Hsiao-Wen Sun, Miaoli County (TW); Hsu-Wen Fu, Kaohsiung (TW); Chia-Hao Chang, Taoyuan (TW)

(73) Assignee: GUANGZHOU TYRAFOS SEMICONDUCTOR TECHNOLOGIES CO., LTD., Guangzhou (CN)

( * ) Notice: Subject to any disclaimer, the term of this patent is extended or adjusted under 35 U.S.C. 154(b) by 819 days.

(21) Appl. No.: 17/731,919

(22) Filed: Apr. 28, 2022

(65) Prior Publication Data

US 2023/0123442 A1 Apr. 20, 2023

Related U.S. Application Data

(60) Provisional application No. 63/255,446, filed on Oct. 14, 2021.

(51) Int. Cl.
*G01N 21/76* (2006.01)
*B01L 3/00* (2006.01)
(Continued)

(52) U.S. Cl.
CPC ........ *G01N 21/76* (2013.01); *B01L 3/502715* (2013.01); *G01N 21/6428* (2013.01); *G01N 21/6454* (2013.01); *G01N 33/54386* (2013.01); *G01N 35/0098* (2013.01); *G01N 35/1011* (2013.01); *H10F 39/182* (2025.01); *H10F 39/199* (2025.01); *H10F 39/8023* (2025.01); *B01L 2200/025* (2013.01); *B01L 2200/10* (2013.01); *G01N 2021/6439* (2013.01); *G01N 2035/103* (2013.01); *G01N 2201/0407* (2013.01)

(58) Field of Classification Search
CPC ............... G01N 21/76; G01N 21/6428; G01N 21/6454; G01N 33/54386; G01N 35/0098; G01N 35/1011; G01N 2021/6439; G01N 2035/103; G01N 2201/0407; G01N 21/645; B01L 3/502715; B01L 2200/025; B01L 2200/10; H10F 39/182; H10F 39/199; H10F 39/8023; H10F 39/8063
See application file for complete search history.

(56) References Cited

U.S. PATENT DOCUMENTS

2002/0081716 A1* 6/2002 Yagi ................ B82Y 30/00
435/287.2
2011/0155891 A1* 6/2011 Yamamoto ............ H10F 39/806
257/E31.127
(Continued)

*Primary Examiner* — Jennifer Wecker
*Assistant Examiner* — Steven Ray Castaneda
(74) *Attorney, Agent, or Firm* — WPAT, PC (57) ABSTRACT

The present invention provides a biomolecule image sensor in which detection molecules are deposed on a light receiving surface of an image sensing element, and method thereof for detecting biomolecule.

3 Claims, 7 Drawing Sheets

(51) Int. Cl.
*G01N 21/64* (2006.01)
*G01N 33/543* (2006.01)
*G01N 35/00* (2006.01)
*G01N 35/10* (2006.01)
*H10F 39/00* (2025.01)
*H10F 39/12* (2025.01)
*H10F 39/18* (2025.01)

(56) References Cited

U.S. PATENT DOCUMENTS

2012/0187516 A1* 7/2012 Sato .................. H01L 24/80
257/E31.124
2016/0381266 A1* 12/2016 Ohmaru ............... H04N 25/708
348/264

* cited by examiner

BIOMOLECULAR IMAGE SENSOR AND METHOD THEREOF FOR DETECTING BIOMOLECULE

CROSS-REFERENCE TO RELATED APPLICATION

This application claims priority of U.S. provisional application No. 63/255,446, filed on Oct. 14, 2021, the content of which is incorporated herein in its entirety by reference.

BACKGROUND OF THE INVENTION

1. Field of the Invention

The present invention relates to a biomolecule image sensor and method thereof for detecting a biomolecule, and more particularly to a biomolecule image sensor with detection molecules arranged on a light receiving surface of a pixel element, and method thereof for detecting biomolecule.

2. The Prior Art

Enzyme-linked immunosorbent assay (ELISA) or enzyme-linked immunoassay (EIA) is the specific antigen-antibody reaction tests. The specific binding properties between antigens and antibodies are used to detect the molecules in samples. The presence of specific antigens or antibodies may be shown by the color reaction with enzymes. Quantitative analysis may be carried out by the depth of color to achieve the detection and screening.

Biochips are micro devices that use biological materials on a substrate to produce specific biochemical reactions with the biomolecules, and may be quantified by a highly sensitive detection system. Biochips provide fast, accurate, and low cost bioanalytical testing capabilities. Biochips are basically miniaturized substrates that may perform hundreds or thousands of biochemical reactions simultaneously.

However, traditional biochemical tests such as on tissue sections require large and expensive equipment to receive optical or electronic signals for analyzing the status of biochemical molecular reactions, for example, observing with microscopes and capturing images with additional photo equipment for further analysis, which require time and manual operations. On the other hand, traditional biochips have to be additionally equipped with other expensive and large image capture systems or equipment to detect and capture the luminescent images of the biochips after the biochemical detection process for subsequent analysis. Further, traditional ELISA has to be equipped with an ELISA reader to detect the absorbance in each well of the microwell plate after the operation with ELISA kit for quantification.

With the increasing popularity of the point of care testing (POCT), a personalized health test with a short analysis time and simple operation, it is necessary to develop a more sensitive and simpler detection device and method to overcome the problems from large equipment and complex biochemical detection processes in traditional biomolecule detection methods.

SUMMARY OF THE INVENTION

One objective of the present invention is to provide a biomolecule image sensor, comprising: an image sensing element, comprising a plurality of unit pixels disposed in an array on a substrate, wherein each of the plurality of unit pixels comprises at least one photoelectric conversion element, the photoelectric conversion element receives an incident light to generate electrons, and a surface of the image sensing element receiving the incident light is defined as a light receiving surface; and a plurality of detection molecules, disposed on the light receiving surface to bind a biomolecule.

In the preferred embodiment of the present invention, the biomolecule image sensor further comprises at least one readout circuit coupled to each of the plurality of unit pixels, and the readout circuit generates a voltage signal based on a number of electrons.

In the preferred embodiment of the present invention, the detection molecules may be disposed corresponding to each of the plurality of unit pixels.

In the preferred embodiment of the present invention, the biomolecule image sensor further comprises a bonding layer disposed on the light receiving surface for binding the detection molecules.

In the preferred embodiment of the present invention, the biomolecule image sensor further comprises a passivation layer disposed between the bonding layer and the light receiving surface for attaching the bonding layer on the light receiving surface.

In the preferred embodiment of the present invention, the bonding layer is disposed to be a plurality of island structures in an array, and each of the plurality of island structures corresponds to each of the plurality of unit pixels.

In the preferred embodiment of the present invention, the island structures may be formed on the light receiving surface by photolithography process or imprint lithography process.

In the preferred embodiment of the present invention, the biomolecule image sensor further comprises a plurality of light blocking layers disposed on the light receiving surface and corresponding to spaces between each of the plurality of unit pixels.

In the preferred embodiment of the present invention, a height of the light blocking layers may be the same as or different from a height of the bonding layer.

In the preferred embodiment of the present invention, the incident light may be a light emitted by a fluorescent marker or a chemiluminescent marker on the biomolecule.

The other objective of the present invention is to provide a method of detecting a biomolecule, comprising: (a) providing the biomolecule image sensor; (b) contacting a sample to the detection molecules to bind the biomolecule in the sample; (c) detecting an incident light by each of the plurality of unit pixels, wherein the incident light comprises a light emitted by a fluorescent marker or a chemiluminescent marker on the biomolecule; (d) generating electrons from the incident light detected by each of the plurality of unit pixels by the photoelectric conversion element; (e) generating a voltage signal based on the number of the electrons by the readout circuit; and (f) analyzing a presence and/or a concentration of the biomolecule based on the voltage signal.

The present invention is a completely innovative image sensor for detecting biomolecules prepared by a semiconductor process. The image sensor of the present invention, which is smaller than a coin, may directly detect the presence of specific biomolecules in samples and quantify concentration thereof, but does not require additional large equipment.

On the other hand, compared with the traditional biochip, the present invention does not require additional image capture system or equipment. That is, the biomolecule image sensor of the present invention provides the functions of biological or chemical analysis and image capture and interpretation. That is, the detection process may be directly operated on the biomolecule image sensor of the present invention, and corresponding detection results may be obtained in real time.

On the other hand, compared with the traditional methods of quantifying biomolecules, the biomolecule image sensor of the present invention independently detects the incident light in the unit through each unit pixel, and compares each measured signal readout with the thresholds independently, and therefore, even when the concentration of the biomolecules in the sample is extremely low, the presence and intensity of chemiluminescent or fluorescent signals of the biomolecules would still be accurately interpreted, so as to increase the detection sensitivity. The biomolecule image sensor of the present invention provides the quantitative mode of analog colorimetric method and digital method, and could be switched according to different concentrations of biomolecules, so as to maximize the detection range.

Further, in the biomolecule image sensor of the present invention, the detection molecules are disposed on the light receiving surface, so that the photoelectric conversion element of the unit pixel in the image sensing element would be very close to the incident light emitted by the biomolecule. Therefore, the photoelectric conversion element could receive the incident light with weak intensity, so that the detection sensitivity of the biomolecule image sensor of the present invention would be improved.

Further, in the biomolecule image sensor of the present invention, since the light blocking layers are formed in the bonding layer corresponding to the spaces between each unit pixel, the photoelectric conversion element could easily determine the incident light really coming from the chemiluminescent marker or the fluorescent marker on the biomolecule. By adjusting the arrangement of the light blocking layers, one single incident light could be received by only one single unit pixel to effectively reduce the mutual interference between the unit pixels.

In order to enable one with ordinary skill in the art to understand the purpose, features, and functions of the present invention, the invention is described in detail below by means of the following specific embodiments and with the attached drawings.

DETAILED DESCRIPTION OF THE PREFERRED EMBODIMENT

The embodiments of the present invention are further described with the following drawings. The following embodiments are given to illustrate the present invention and are not intended to limit the scope of the present invention, and one with ordinary skill in the art may make some modifications and refinements without departing from the spirit and scope of the present invention. Therefore, the scope of the present invention is defined by the scope of the appended claims.

The terms used herein are only for describing the embodiments, and are not intended to limit the present invention. Unless otherwise defined, the terms have meanings commonly understood by one with ordinary skill in the art to which the present invention belongs. As used herein, the singular forms "a" and "the" are intended to include the plural forms as well, unless the context clearly indicates otherwise. As used herein, the term "and/or" includes any and all combinations of one or more of the associated listed items.

Similarly, when an element is referred to be "on" or "above" another element, it would be understood that the element may be directly on the other element or intermediate elements may be present. In contrast, the term "directly" represents that there is no intermediate element. The term "comprising" used herein should be understood to indicate the presence of stated features, integers, steps, operations, elements, and/or components, but not exclude the presence or addition of one or more other features, integers, steps, operations, elements, components, and/or any combination thereof.

According to the present invention, the operating procedures and parameter conditions for enzyme-linked immunosorbent assay (ELISA) are within the professional literacy and routine techniques of one with ordinary skill in the art.

According to the present invention, the fluorescent molecules may be, but not limited to, FITC, HEX, FAM, TAMRA, Cy3, Cy5, quantum dot, or the like.

FIGS. 1 to 5 show the biomolecule image sensor according to various embodiments of the present invention. As shown in FIGS. 1 to 5, the biomolecule image sensor of the present invention comprises an image sensing element 10 and a plurality of detection molecules 21, and may further comprise at least one readout circuit; wherein, the image sensing element 10 may include a plurality of unit pixels 11 disposed in an array on a substrate; further, the detection molecules 21 may be used to bind a biomolecule (not shown in FIGS.). For example, the detection molecule may be a ligand, and the biomolecule may be a corresponding receptor. Alternatively, the detection molecule may be a receptor, and the biomolecule may be a corresponding ligand. The interaction between such receptors and ligands may be antigen-antibody, enzyme-substrate, DNA-RNA hybridization, and the like reactions.

More specifically, the image sensing element 10 in the biomolecule image sensor according to the present invention may be a back-illuminated complementary metal-oxidesemiconductor (CMOS) image sensor or a front-illuminated CMOS image sensor; however, the present invention is not limited thereto.

In the embodiments of the present invention, each of the unit pixels 11 may include at least one photoelectric conversion element, wherein the photoelectric conversion element may generate electrons after receiving an incident light, and the photoelectric conversion element also includes the ability to accumulate the aforementioned electrons; however, the present invention is not limited to thereto.

Further, the photoelectric conversion element may be an element that generates and accumulates electrons corresponding to the incident light. For example, the photoelectric conversion element may be a photodiode, a photo transistor, a photo gate, a pinned photo diode (PPD), an avalanche photodiode (APD), a single-photon avalanche diode (SPAD), a photomultiplier tube (PMT), or any combination thereof.

Further, the detection molecules 21 may be molecules with selective and/or specific binding ability to specific molecules. In the preferred embodiments of the present invention, the detection molecules 21 may be, but not limited to, an antibody or an aptamer.

In the embodiments of the present invention, a surface of the image sensing element 10 receiving the incident light may be defined as a light receiving surface 12, and the detection molecules 21 may be disposed on the light receiving surface 12. The light receiving surface 12 provides the characteristics of high light transmittance and small extinction coefficient. Further, a protective layer may be further formed on the light receiving surface 12, preferably composed of $SiO_2$. The protective layer may prevent external factors such as oxidation, dust, scratches, water, and the like from damaging the unit pixels 11 or other components on the image sensing element 10.

In one preferred embodiment of the present invention, the detection molecules 21 may be centrally disposed corresponding to the unit pixels 11, especially the photoelectric conversion elements therein. In this way, when the photoelectric conversion elements in the unit pixels 11 receive the incident light, the sensitivity of detecting the light emitted from the positions of the detection molecules 21 may be improved, and the mutual interference between the unit pixels 11 may also be reduced.

In the embodiments of the present invention, the readout circuits may be coupled to the unit pixels 11 and generate a voltage signal, which is used as the signal readout, according to the number of the electrons generated after the photoelectric conversion element receives the incident light.

Figure 1:
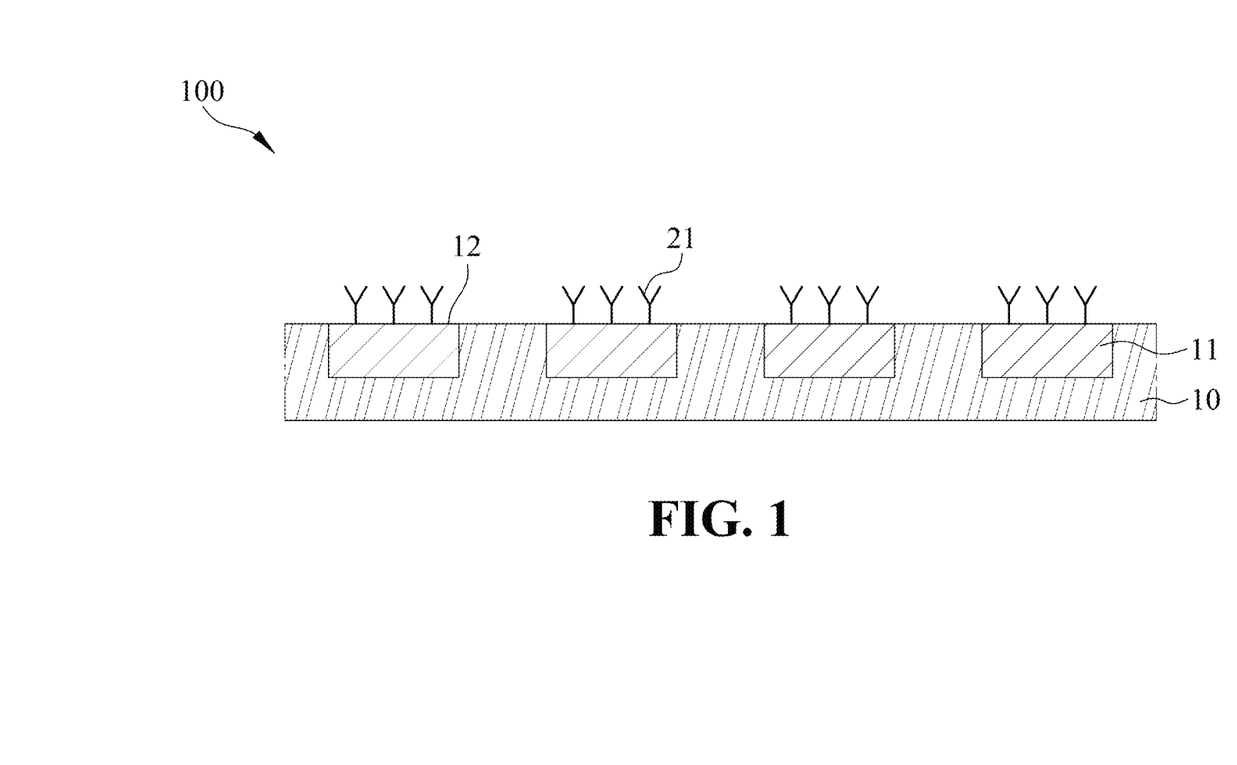
FIG. 1 shows a cross-section view of the biomolecule image sensor according to one embodiment of the present invention.

In one preferred embodiment of the present invention, as shown in FIG. 1, the image sensing element 10 in the biomolecule image sensor 100 according to the present invention may be a CMOS image sensor obtained by a semiconductor process. The surface thereof may be oxidized to form a light transmitting flat surface composed of $SiO_2$ after the packaging process. The flat surface may be the aforementioned protective layer on the light receiving surface 12 for receiving incident lights.

Then, chemical modification methods may be used to fix a plurality of the detection molecules 21 directly on the light receiving surface 12. For example, the oxygen atoms in the silica of the light receiving surface 12 may be used. The light receiving surface 12 is modified with a silane compound such as (3-aminopropyl)triethoxysilane (APTES) to encompass an amino group ($NH_2$), so as to generate bonds with the detection molecules 21 such as antibodies, receptor proteins, DNA, aptamers, or other chemical molecules. Therefore, the detection molecules 21 could be directly immobilized on the light receiving surface 12 of the image sensing element 10.

More specifically, EDC/NHS reaction may be used to form chemical bonding between the carboxyl group on the antibody used as the detection molecule 21 and the amine group on the light receiving surface 12, so as to immobilize the detection molecule 21 on the light receiving surface 12. Alternatively, glutaraldehyde may be used to link both of the protein G and the amine group on the light receiving surface 12. Since protein G could bind to the Fc region of most antibodies, the antibody used as the detection molecule 21 may be flexibly changed according to different biomolecules.

Figure 2:
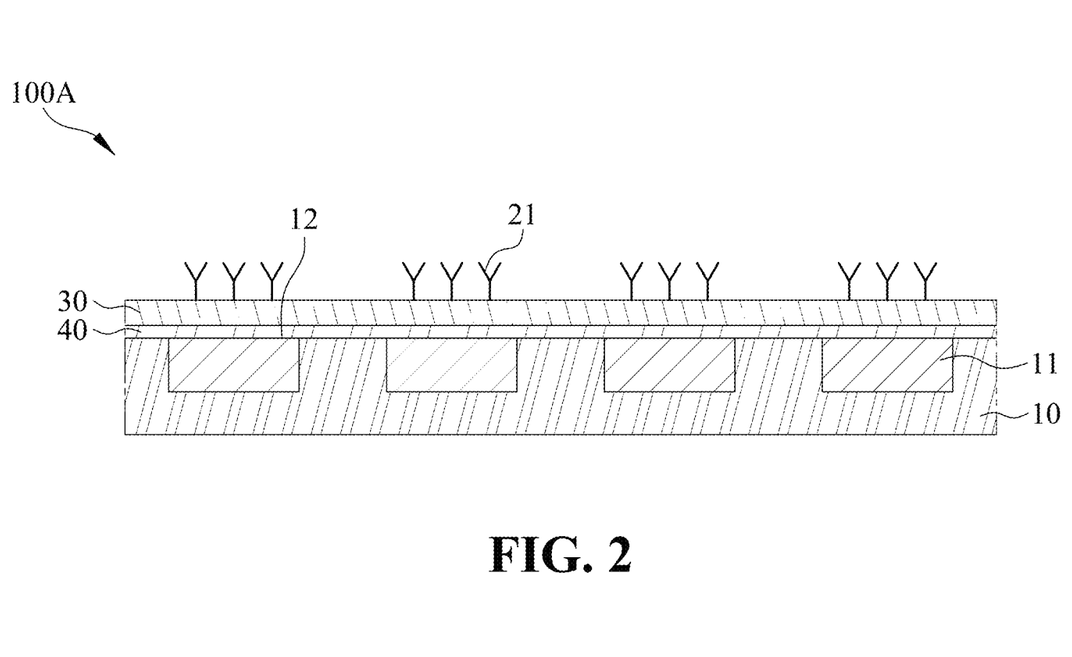
FIG. 2 shows a cross-section view of the biomolecule image sensor according to another embodiment of the present invention, which further comprises a bonding layer."

In another preferred embodiment of the present invention, as shown in FIG. 2, in order to dispose the detection molecules 21 more easily on the light receiving surface 12, in the biomolecule image sensor 100A of the present invention, a bonding layer 30 may be further included between the light receiving surface 12 and the detection molecules 21, and the detection molecules 21 are directly disposed on (bind to) the bonding layer 30. In the embodiments of the present invention, the bonding layer 30 may be composed of the following materials, but not limited to: $SiO_2$, polyimide (PI), poly(methyl methacrylate) (PMMA), polyethylene terephthalate (PET), polystyrene (PS), polydimethylsiloxane (PDMS), epoxy, and the like.

Further, in order to attach the bonding layer 30 more easily and firmly on the light receiving surface 12, a passivation layer 40 may be further included between the light receiving surface 12 and the bonding layer 30. In the embodiments of the present invention, the passivation layer 40 may be composed of the following materials, but not limited to: indium tin oxide (ITO), $SnO_2$, $ZnSnO_2$ (ITO; wherein Zn and Sn may be other atoms), $In_2O_3$, silicon nitride, and the like. One with ordinary skill the art of the present invention could select a suitable material to prepare the passivation layer 40 according to the material of the bonding layer 30."

Figure 3:
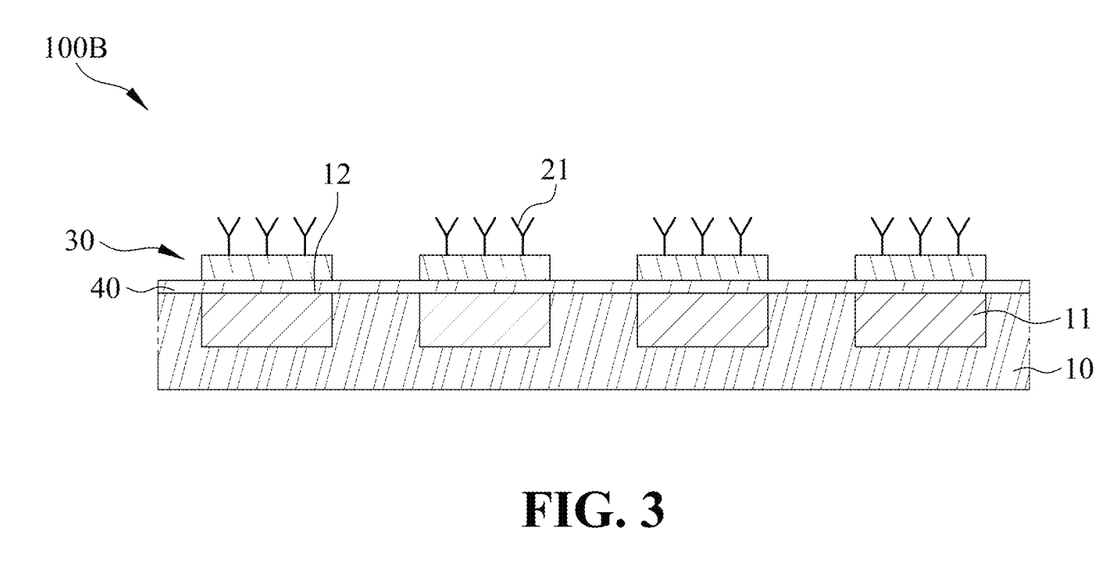
FIG. 3 shows a cross-section view of the biomolecule image sensor according to another embodiment of the present invention, wherein the bonding layer forms a plurality of island structures.

In another preferred embodiment of the present invention, as shown in FIG. 3, in the biomolecule image sensor 100B of the present invention, the bonding layer 30 may be disposed to be a plurality of island structures in an array, and each of the island structures may correspond to the unit pixel 11, preferably correspond to the photoelectric conversion elements in the unit pixel 11. More specifically, a semiconductor process, such as photolithography process or imprint lithography process, may be used to dispose the bonding layer 30 to be a plurality of the island structures on the light receiving surface 12, and a passivation layer 40 may be further included between the light receiving surface 12 and the bonding layer 30.

More specifically, since each of the island structures in the bonding layer 30 directly corresponds to the unit pixel 11, the detection molecules 21 disposed on the bonding layer 30 would be centrally disposed on the unit pixels 11. Therefore, when the photoelectric conversion elements in the unit pixels 11 receive the incident light, the incident light emitted from the positions of the detection molecules 21, such as chemiluminescence or fluorescence emitted by the biomolecules bound to the detection molecules 21, may be received centrally. Since the distance between the incident light and the photoelectric conversion element is short, the photoelectric conversion element could receive the incident light even the intensity of the incident light is weak, thus improving the sensitivity of detecting specific biomolecules in the test sample.

Figure 4:
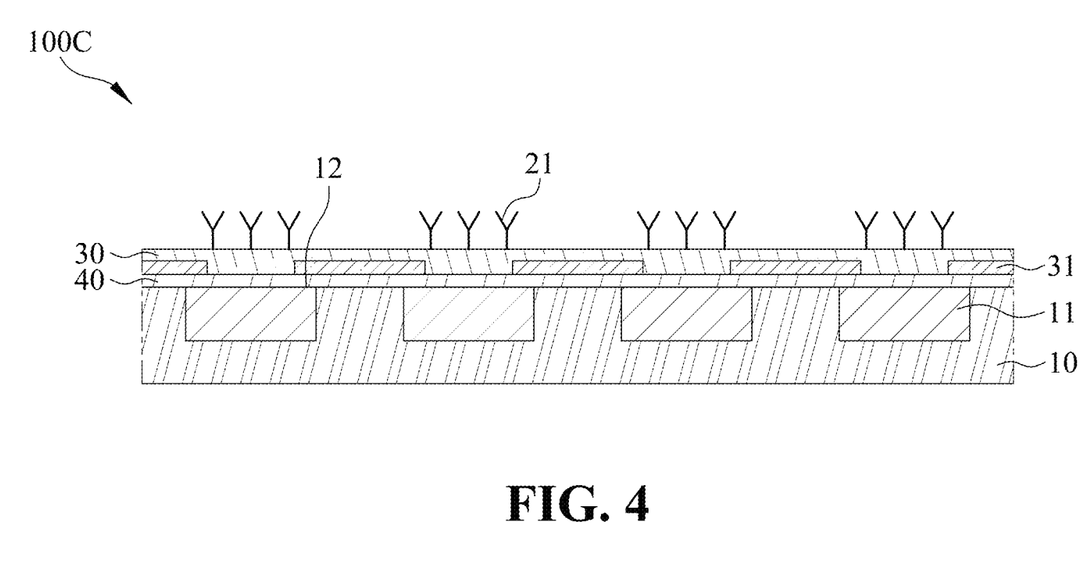
FIG. 4 shows a cross-section view of the biomolecule image sensor according to another embodiment of the present invention, wherein the bonding layer further contains a plurality of light blocking layers.

In another preferred embodiment of the present invention, as shown in FIG. 4, in the biomolecule image sensor 100C of the present invention, the bonding layer 30 may further include a plurality of light blocking layers 31. The light blocking layers 31 may be disposed in an array on the light receiving surface 12 and correspond to spaces between the unit pixels 11 to reduce the mutual interference between the unit pixels 11. More specifically, in order to prevent one single incident light from being received by two or more unit pixels 11 at the same time, that is, one single incident light could only be received by one single unit pixel 11, the light blocking layers 31 may be disposed in the bonding layer 30 corresponding to the spaces between the unit pixels 11 to avoid mutual interference between the light receiving area of each unit pixel 11. The light blocking layers 31 may be composed of light absorbing substances; more specifically, a black photoresist, a metal, or a metal compound such as $CrO_3$, but the present invention is not limited thereto.

Further, according to the relationship between the unit pixels 11, the size, spacing, and/or arrangement of the light blocking layers 31 may be adjusted. For example, a width of the light blocking layers 31 may be greater than a width of the space between the unit pixels 11. That is, the light blocking layers 31 may slightly cover part of the edges of the unit pixels 11. Such arrangement of the light blocking layers 31 could cause the opening of the light receiving area of each unit pixel 11 smaller than the area of the unit pixels 11 themselves to effectively reduce the mutual interference between the unit pixels 11.

Figure 5:
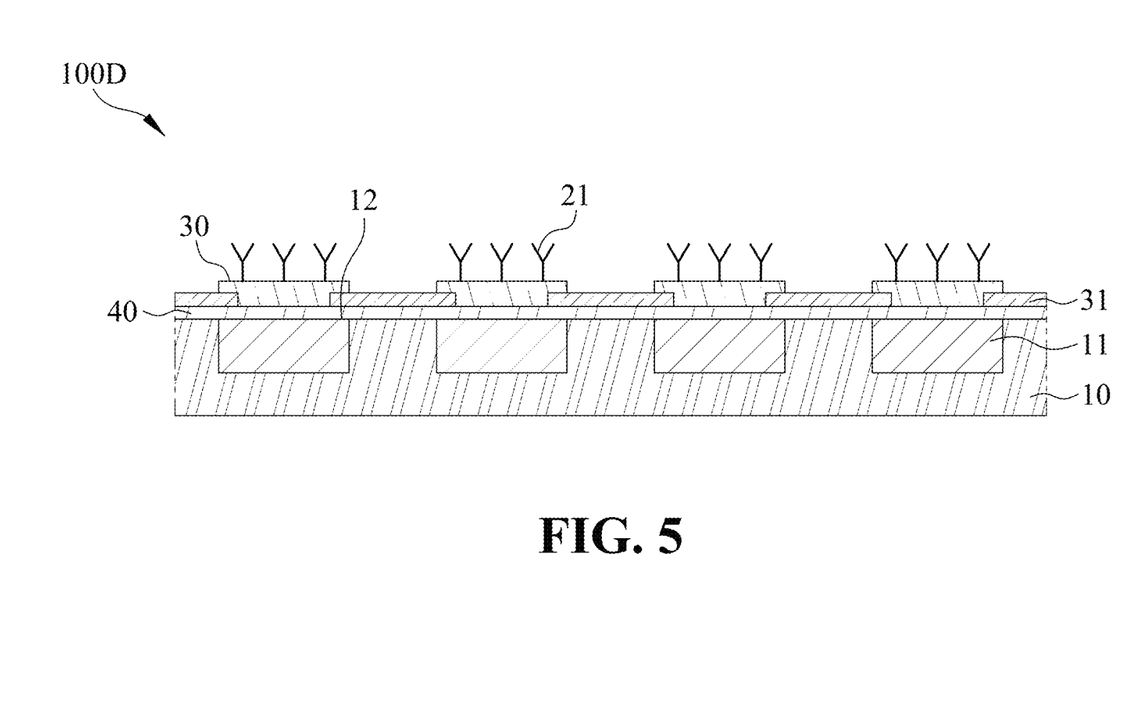
FIG. 5 shows a cross-section view of the biomolecular biomolecule image sensor according to another embodiment of the present invention, wherein the bonding layer forms a plurality of island structures and contains a plurality of light blocking layers.

In another preferred embodiment of the present invention, as shown in FIG. 5, similar to the biomolecule image sensor 100C of the present invention shown as FIG. 4, in the biomolecule image sensor 100D of the present invention, the bonding layer 30 may be disposed to be the aforementioned island structures by a semiconductor process such as photolithography process, and further a height of each of the plurality of island structures is greater than a height of the plurality of light blocking layers 31, a top portion of each of the plurality of island structures extends to a top portion of each of the plurality of light blocking layers 31, the plurality of island structures are separated from each other, and an surface area of the top portion of each of the plurality of island structures equals to a surface area of each of the plurality of unit pixels 11. Therefore, the detection molecules 21 are more concentrated and closer to the image sensing element 10, and the light emitted by the biomolecules bound thereon is more easily received by the photoelectric conversion element in the unit pixel 11.

The biomolecule image sensor of the present invention is not limited to any specific applications. In one preferred embodiment, the biomolecule image sensor of the present invention is used for biological or chemical analysis, such as detecting the presence and/or concentration of a biomolecule in a sample. That is, the incident light may be a light emitted by a fluorescent marker, a reporter marker, or a chemiluminescent marker of the biomolecule. More specifically, when the biomolecule image sensor 100 of the present invention is used to detect the biomolecule A, in the biological or chemical analysis process, the biomolecule A may undergo luminescence reaction with other molecules and emit an incident light such as chemiluminescence or fluorescence. Further, the biomolecule A may be a protein, a peptide, an antibody, a nucleic acid, or the like.

Further, such biological or chemical analysis and luminescence reactions may be performed on the biomolecule image sensor of the present invention, and the image sensing element 10 may directly detect the presence and/or concentration of the biomolecule. For example, ELISA may be performed on the biomolecule image sensor of the present invention. The biomolecules are bound to the detection molecules 21, and a luminescence reaction is performed to generate a chemiluminescence, which is the incident light received by the photoelectric conversion element in the unit pixel 11.

Figure 6A:
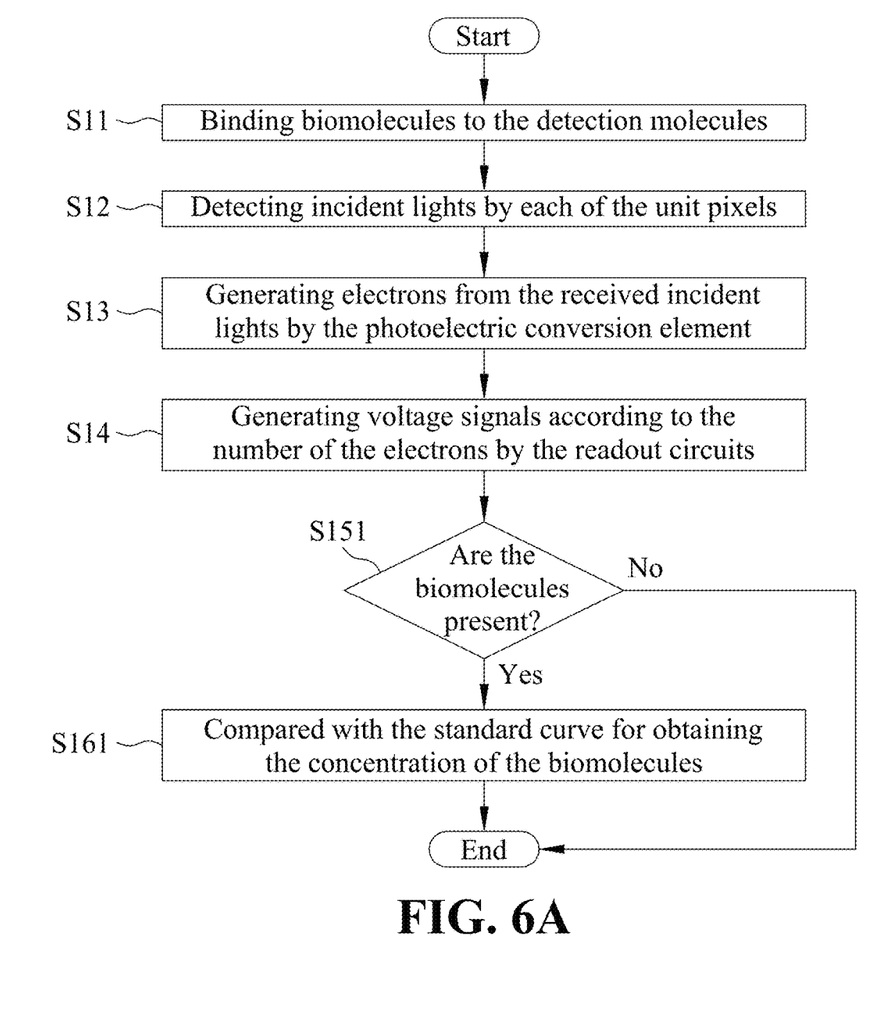
FIG. 6A shows a flowchart of the method of detecting biomolecule through the biomolecular image sensor according to one embodiment of the present invention.
Figure 6B:
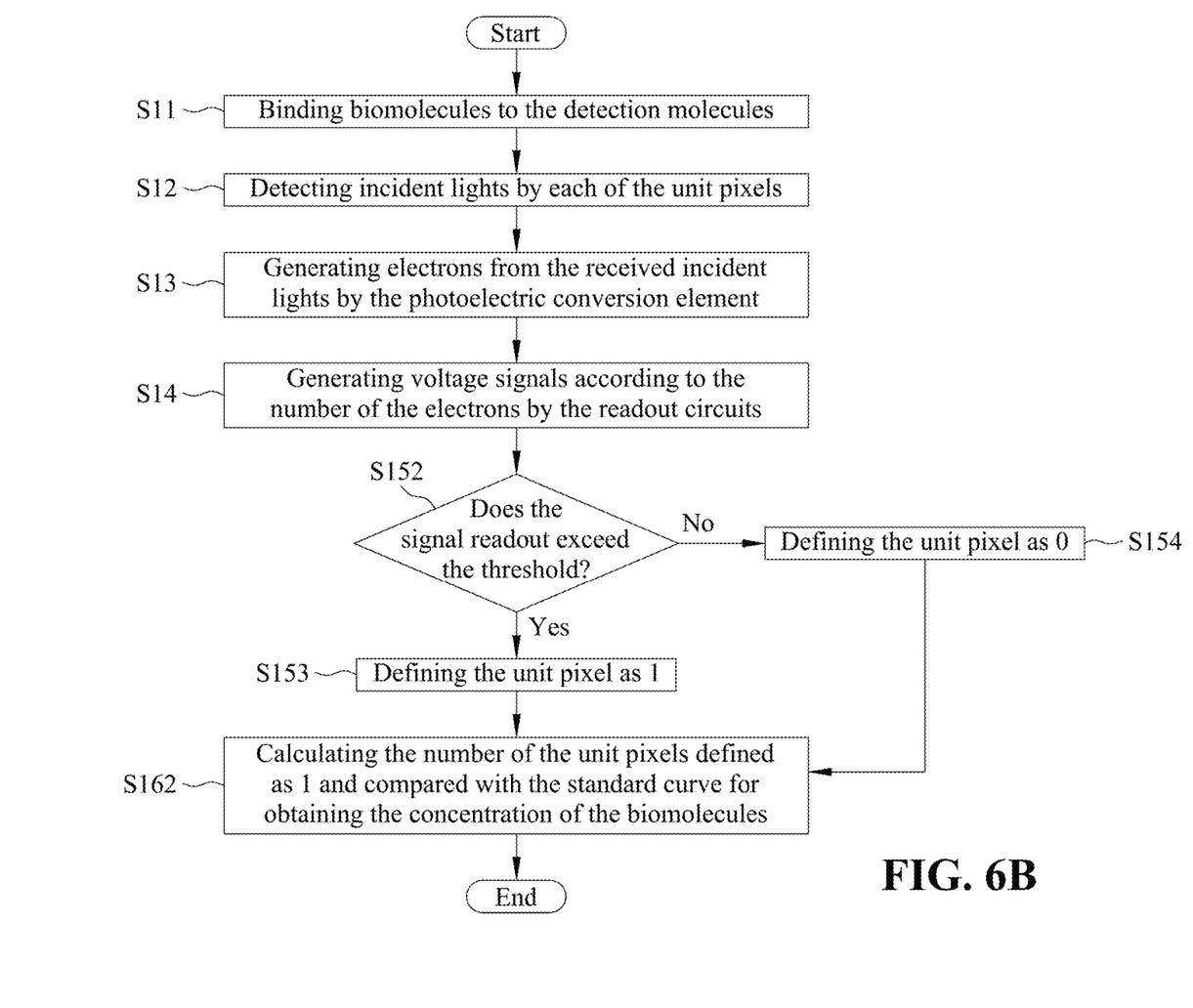
FIG. 6B shows a flowchart of the method of detecting biomolecule through the biomolecular image sensor according to another embodiment of the present invention.

More specifically, as shown in FIGS. 6A and 6B, the method of detecting a biomolecule in a sample by the biomolecule image sensor of the present invention may be as following. The biomolecule in the sample is bond to the detection molecules 21 through biological or chemical analysis such as ELISA (S11). The incident light is detected by the unit pixels respectively (S12), wherein the incident light includes the lights emitted by the fluorescent maker or the chemiluminescent marker of the biomolecule. Electrons are generated from the incident light received by each of the unit pixels through the photoelectric conversion element (S13). A voltage signal is generated according to the number of the electrons through the readout circuits (S14). The presence and/or concentration of the biomolecule are then analyzed according to the voltage signal.

Alternatively, the biomolecule may be detected by an antibody or aptamer labeled with a fluorescent molecule. A radiated light is generated by irradiating excitation light with a specific wavelength, and the radiated light is the incident light received by the photoelectric conversion element in the unit pixel 11. Antibodies or aptamers labeled with different fluorescent molecules may be used as the detection molecules 21, so that the detection of various target biomolecules may be performed on the same sample during one single detection. Further, a CMOS image sensor with RGB technology may be used for antibodies or aptamers including multiple fluorescent labels.

When the biomolecule image sensor of the present invention is used to detect the presence and/or concentration of the biomolecule, the quantification thereof may be not only performed by analog colorimetric method, that is, the incident light received by the unit pixels 11 is one single readout to determine the presence of the biomolecule (S151) or further compare with the standard curve for obtaining the concentration of the biomolecule (S161), but also by digital method, that is, according to the predetermined threshold (S152), the unit pixels 11 with the signal readout exceeding the threshold are defined as 1 (S153) and the unit pixels 11 with the signal readout not exceeding the threshold are defined as 0 (S154), and the number of unit pixels 11 defined as 1 is calculated and compared with the standard curve (S162) to obtain the concentration of the biomolecule more accurately.

Further, traditional ELISA utilizes large and expensive equipment to receive optical or electrical signals after performing complex biochemical detection procedures to analyze the status of biochemical molecular reactions. The present invention is a completely innovative image sensor for detecting biomolecules prepared by a semiconductor process. The image sensor of the present invention, which is smaller than a coin, may directly detect the presence of specific biomolecules in samples and quantify concentration thereof, but does not require additional large equipment.

On the other hand, compared with the traditional biochip, the present invention does not require additional image capture system or equipment. That is, the biomolecule image sensor of the present invention provides the functions of biological or chemical analysis and image capture and interpretation. That is, the detection process may be directly operated on the biomolecule image sensor of the present invention, and corresponding detection results may be obtained in real time.

On the other hand, when quantifying biomolecule images by traditional methods, such as observation with a microscope, if the concentration of the biomolecules is extremely low, the biomolecules directly placed on the surface of the glass slide would distribute extremely uneven, resulting that only a small part of the area includes chemiluminescent or fluorescent signals, and therefore, the presence and intensity of the optical signals cannot be effectively interpreted within the overall field of view, so as to decrease the detection sensitivity. However, the biomolecule image sensor of the present invention independently detects the incident light in the unit through each unit pixel, and compares each measured signal readout with the thresholds independently, and therefore, even when the concentration of the biomolecules in the sample is extremely low, the presence and intensity of chemiluminescent or fluorescent signals of the biomolecules would still be accurately interpreted, so as to increase the detection sensitivity. The biomolecule image sensor of the present invention provides the quantitative mode of analog colorimetric method and digital method, and could be switched according to different concentrations of biomolecules, so as to maximize the detection range.

Further, in the biomolecule image sensor of the present invention, the detection molecules are disposed on the light receiving surface, so that the photoelectric conversion element of the unit pixel in the image sensing element would be very close to the incident light emitted by the biomolecule. Therefore, the photoelectric conversion element could receive the incident light with weak intensity, so that the detection sensitivity of the biomolecule image sensor of the present invention would be improved.

Further, in the biomolecule image sensor of the present invention, since the light blocking layers are formed in the bonding layer corresponding to the spaces between each unit pixel, the photoelectric conversion element could easily determine the incident light really coming from the chemiluminescent marker or the fluorescent marker on the biomolecule. By adjusting the size, spacing and/or arrangement of the light blocking layers, one single incident light could be received by only one single unit pixel to effectively reduce the mutual interference between the unit pixels.

What is claimed is:

1. A biomolecule image sensor, comprising:
   an image sensing element, comprising a plurality of unit pixels disposed in an array on a substrate, wherein each of the plurality of unit pixels comprises at least one photoelectric conversion element, the photoelectric conversion element configured to receive an incident light to generate electrons, and a surface of the image sensing element configured to receive the incident light, wherein the surface of the image sensing element is defined as a light receiving surface;
   a passivation layer, disposed on the light receiving surface;
   a bonding layer, disposed on the passivation layer, disposed to be a plurality of island structures in an array, and each of the plurality of island structures corresponding to each of the plurality of unit pixels;
   a plurality of light blocking layers, disposed on the passivation layer and corresponding to spaces between each of the plurality of unit pixels;
   a plurality of detection molecules, disposed on the bonding layer, and configured to contact a sample to the detection molecules to bind a biomolecule in the sample;
   and at least one readout circuit, coupled to each of the plurality of unit pixels, and configured to generate a voltage signal based on a number of electrons;
   wherein a height of each of the plurality of island structures is greater than a height of the plurality of light blocking layers, a top portion of each of the plurality of island structures extends to a top portion of each of the plurality of light blocking layers, the plurality of island structures are separated from each other, and a surface area of the top portion of each of the plurality of island structures equals to a surface area of each of the plurality of unit pixels;
   wherein each of the plurality of unit pixels is configured to detect the incident light, the incident light comprises a light emitted by a fluorescent marker or a chemiluminescent marker on the biomolecule, the incident light detected by each of the plurality of unit pixels configured to generate electrons by the photoelectric conversion element, the readout circuit configured to generate a voltage signal based on the number of the electrons and analyze a presence or a concentration of the biomolecule based on the voltage signal;
   wherein when the biomolecule image sensor is configured to be used to detect the presence and/or concentration of the biomolecule, a quantification is configured to be performed by an analog colorimetric method or by a digital method;
   wherein the analog colorimetric method is defined as follows: the incident light received by the unit pixels is one single readout configured to determine the presence of the biomolecule or further compare with a standard curve in order to obtain the concentration of the biomolecule; and
   wherein the digital method is defined as follows: according to a predetermined threshold, the unit pixels with the signal readout exceeding the predetermined threshold are defined as 1 and the unit pixels with the signal readout not exceeding the predetermined threshold are defined as 0, and the number of unit pixels defined as 1 is configured to be calculated and compared with the standard curve in order to obtain the concentration of the biomolecule more accurately.

2. The biomolecule image sensor according to claim 1, wherein the island structures are formed on the light receiving surface by photolithography process or imprint lithography process.

3. The biomolecule image sensor according to claim 1, wherein a width of the light blocking layers is greater than a width of spaces between each of the plurality of unit pixels.

* * * * *